(12) United States Patent
Muehlberg et al.

(10) Patent No.: US 11,954,178 B2
(45) Date of Patent: Apr. 9, 2024

(54) METHOD AND DATA PROCESSING SYSTEM FOR PROVIDING EXPLANATORY RADIOMICS-RELATED INFORMATION

(71) Applicant: Siemens Healthcare GmbH, Erlangen (DE)

(72) Inventors: Alexander Muehlberg, Nuremberg (DE); Oliver Taubmann, Weilersbach (DE); Alexander Katzmann, Fuerth (DE); Felix Durlak, Langenzenn (DE); Michael Wels, Bamberg (DE); Felix Lades, Erlangen (DE); Rainer Kaergel, Stegaurach (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 260 days.

(21) Appl. No.: 17/462,140

(22) Filed: Aug. 31, 2021

(65) Prior Publication Data

US 2022/0101070 A1  Mar. 31, 2022

(30) Foreign Application Priority Data

Sep. 30, 2020 (EP) .................................... 20199387

(51) Int. Cl.
*G06F 18/2433* (2023.01)
*G06F 18/21* (2023.01)
(Continued)

(52) U.S. Cl.
CPC ...... *G06F 18/2433* (2023.01); *G06F 18/2193* (2023.01); *G06F 18/245* (2023.01);
(Continued)

(58) Field of Classification Search
None
See application file for complete search history.

(56) References Cited

U.S. PATENT DOCUMENTS

2017/0358079 A1* 12/2017 Gillies .................. A61B 6/469
2020/0005461 A1*  1/2020 Yip ........................ A61B 5/725
(Continued)

OTHER PUBLICATIONS

Gillies RJ, Kinahan PE, Hricak H. Radiomics: Images Are More than Pictures, They Are Data. Radiology. Feb. 2016;278(2):563-77. doi: 10.1148/radiol.2015151169. Epub Nov. 18, 2015. PMID: 26579733; PMCID: PMC4734157. Available online: https://www.ncbi.nlm.nih.gov/pmc/articles/PMC4734157/ (Year: 2016).*

(Continued)

*Primary Examiner* — Tahmina N Ansari
(74) *Attorney, Agent, or Firm* — Harness, Dickey & Pierce, P.L.C.

(57) ABSTRACT

A computer-implemented method is for providing radiomics-related information. In an embodiment, the computer-implemented method includes receiving radiomics-related data; determining, based on the radiomics-related data and an assistance algorithm, a function for processing the radiomics-related data; calculating, based on the radiomics-related data and the function for processing the radiomics-related data, the radiomics-related information; and providing the radiomics-related information.

25 Claims, 6 Drawing Sheets

(51) Int. Cl.
*G06F 18/245* (2023.01)
*G06T 7/00* (2017.01)

(52) U.S. Cl.
CPC .. *G06T 7/0012* (2013.01); *G06T 2207/20076* (2013.01); *G06V 2201/03* (2022.01)

(56) References Cited

U.S. PATENT DOCUMENTS

| | | | |
|---|---|---|---|
| 2020/0015734 A1* | 1/2020 | Mayer | G06T 7/62 |
| 2020/0126663 A1* | 4/2020 | Lucas | G06V 30/418 |
| 2021/0166389 A1* | 6/2021 | Denzinger | G06T 7/62 |
| 2022/0101070 A1* | 3/2022 | Muehlberg | G06F 18/2193 |
| 2022/0328189 A1* | 10/2022 | Zhou | G06V 10/26 |

OTHER PUBLICATIONS

Schulz, K. et. al., "CONSORT 2010 statement: updated guidelines for reporting parallel group randomised trials", BMC medicine 8.1: 18, 2010.

Olson, R. et. al., "TPOT: A tree-based pipeline optimization tool for automating machine learning", Automated Machine Learning, Springer, pp. 151-160, 2019.

Feurer, M. et. al., "Auto-sklearn: efficient and robust automated machine learning. Automated Machine Learning", Springer, pp. 113-134, 2019.

Lambin, P. et. al., "Radiomics: the bridge between medical imaging and personalized medicine", Nature reviews Clinical oncology 14.12: 749, 2017.

Wels, M. et. al., "General purpose radiomics for multi-modal clinical research", Medical Imaging 2019: Computer-Aided Diagnosis, vol. 10950, International Society for Optics and Photonics, 2019.

Noble, W., "How does multiple testing correction work?", Nature biotechnology 27.12: 1135-1137, 2009.

Extended European Search Report dated Mar. 18, 2021.

* cited by examiner

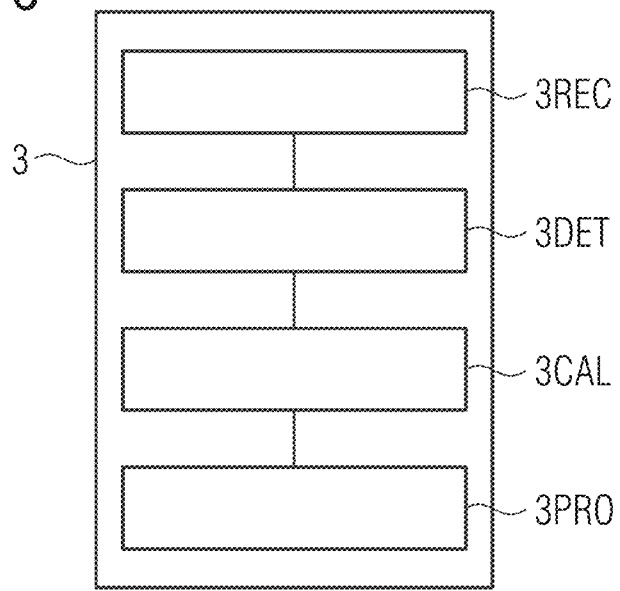

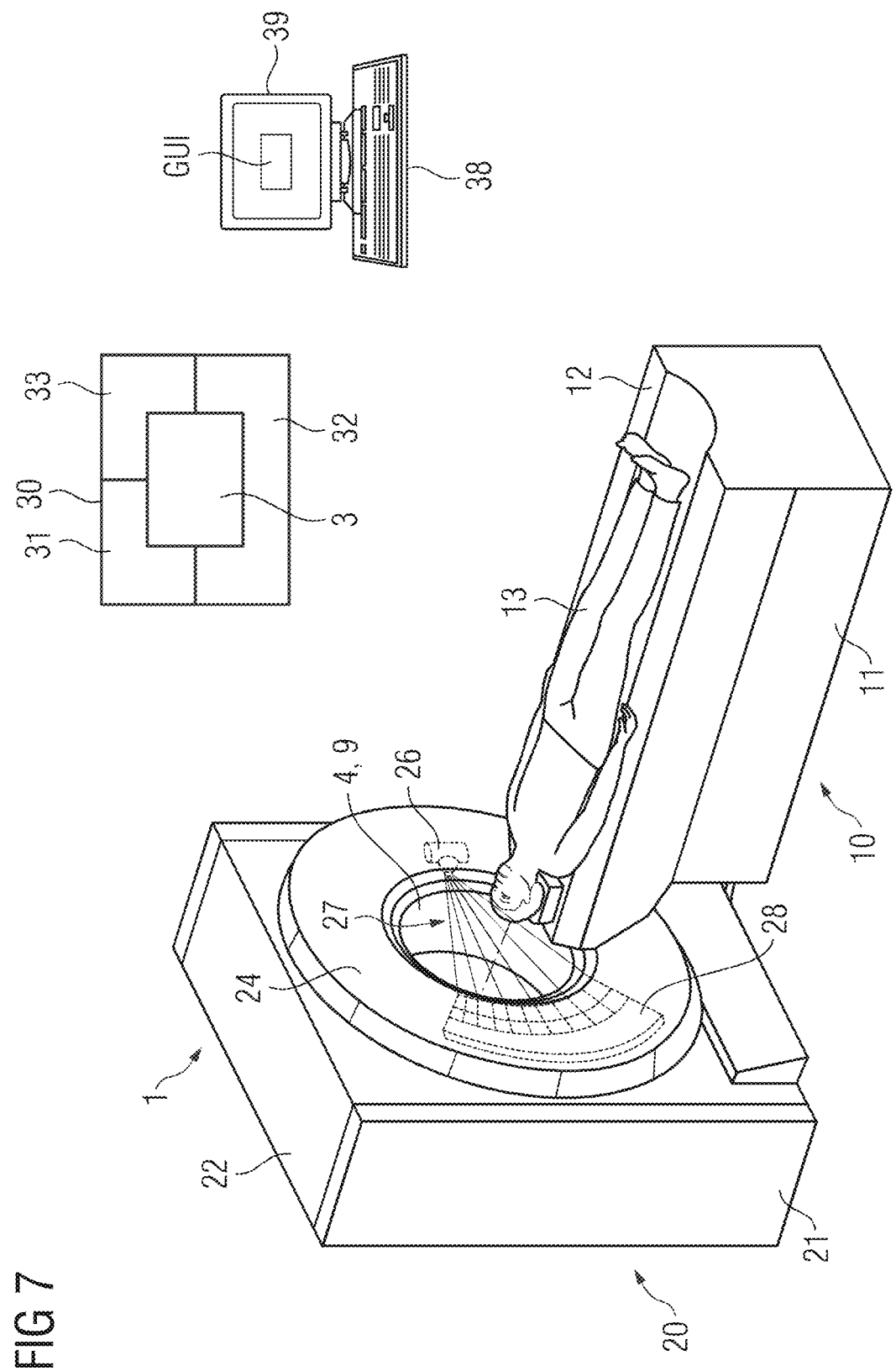

METHOD AND DATA PROCESSING SYSTEM FOR PROVIDING EXPLANATORY RADIOMICS-RELATED INFORMATION

PRIORITY STATEMENT

The present application hereby claims priority under 35 U.S.C. § 119 to European patent application number EP 20199387.0 filed Sep. 30, 2020, the entire contents of which are hereby incorporated herein by reference.

FIELD

Example embodiments of the invention generally relate to a method for providing radiomics-related information; to a data processing system; to a computer program product; and to a computer-readable medium.

BACKGROUND

Radiomics is one of the most important state-of-the-art approaches in current clinical research with regards to quantitative radiological biomarker discovery. These biomarkers, i.e., features, offer a huge, mostly untapped potential and can be combined with other biomarkers to foster precision medicine. Various tools exist that allow customers without in-depth technical knowledge (such as radiologists) to perform radiomics analysis on their own data.

However, due to the vast number of features involved in such analyses as well as their interactions, statistical expertise is crucial for correctly analyzing these studies, identifying meaningful connections in the data and properly presenting these results in peer-reviewed publications. Statistical analysis methods always entail the risk to mistakenly consider found associations meaningful in case the data at hand does not fulfill important prerequisites. This complexity increases further when other, non-imaging-based biomarkers, e.g. other high-dimensional "omics" data, are included in the analysis as well, which is considered a highly desirable goal for designing comprehensive clinical decision support systems.

Typically, statistical and machine learning expertise is scarce, which can severely harm the scientific quality of studies and prevent many investigations from yielding useful, reproducible results or even from being performed at all. Therefore there are companies which offer the correct execution of a study as a service, but also professions in the pharmaceutical industry (clinical monitor), as they have a special interest in the correct execution of the study in order to be able to assess the effectiveness of their drugs.

In addition, the amount of research, labor and time that is currently required from customers for publications is substantial.

Also, novel technologies are often not promoted correctly, either because of a lack of statistical experience, but also a correct study design to evaluate the value of the technology is not known. This an indirectly harm the advertisement of a novel technology such as photon counting. An automated and correct analysis can therefore be an accelerant for the distribution and establishment of these novel imaging technologies.

Finally, and most importantly, multispectral imaging as a novel technology profits from high-quality studies that are published in high-impact factor journals. These studies are often not conducted well, either because of a lack of statistical and/or machine learning knowledge but also from missing experience how to elaborate the additional value of these technologies. Also, the manuscript can often take a long time until it is published and much effort from e.g. global collaboration managers must be spent.

SUMMARY

Our approach, in at least one embodiment, offers the opportunity to train clinicians in the use of new technologies such as photon counting or general multispectral imaging and can lead them through the process of correct study design, correct use of technology and correct analysis with one software solution.

Our approach, in at least one embodiment, offers the opportunity to acquire the required statistical knowledge themselves through reading associated literature. This is very time-consuming (and therefore prohibitive for most radiologists due to the demands of daily routine) and has many pitfalls when only superficial, incomplete knowledge is achieved.

In one embodiment, the invention relates to a computer-implemented method for providing radiomics-related information, the method comprising
receiving radiomics-related data,
determining, based on the radiomics-related data and an assistance algorithm, a function for processing the radiomics-related data,
calculating, based on the radiomics-related data and the function for processing the radiomics-related data, the radiomics-related information, and
providing the radiomics-related information.

In another embodiment the invention relates to data processing system for providing radiomics-related information, comprising
a receiving interface, configured for receiving radiomics-related data,
a determining unit, configured for determining, based on the radiomics-related data and an assistance algorithm, a function for processing the radiomics-related data,
a calculating unit, configured for calculating, based on the radiomics-related data and the function for processing the radiomics-related data, the radiomics-related information,
a providing interface, configured for providing the radiomics-related information.

In another embodiment the invention relates to a computer program comprising instructions which, when the program is executed by a data processing system, cause the data processing system to carry out the method of one of the disclosed embodiments.

In another embodiment the invention relates to a computer-readable medium comprising instructions which, when executed by a data processing system, cause the system to carry out the method of one of the disclosed embodiments.

In another embodiment the invention relates to a computer-implemented method for providing radiomics-related information, the computer-implemented method comprising
receiving radiomics-related data;
determining, based on the radiomics-related data and an assistance algorithm, a function for processing the radiomics-related data;
calculating, based on the radiomics-related data and the function for processing the radiomics-related data, the radiomics-related information; and
providing the radiomics-related information.

In another embodiment the invention relates to a data processing system for providing radiomics-related information, comprising:

a receiving interface, configured for receiving (REC) to receive radiomics-related data;

a determining unit, configured to determine, based on the radiomics-related data and an assistance algorithm, a function for processing the radiomics-related data;

a calculating unit, configured to calculate, based on the radiomics-related data and the function for processing the radiomics-related data, the radiomics-related information; and a providing interface, configured to provide the radiomics-related information.

In another embodiment the invention relates to a non-transitory computer program product storing instructions which, when the program is executed by a data processing system, cause the data processing system to carry out the method of an embodiment.

In another embodiment the invention relates to a non-transitory computer-readable medium storing instructions which, when executed by a data processing system, cause the system to carry out the method of an embodiment.

BRIEF DESCRIPTION OF THE DRAWINGS

The invention will be illustrated below with reference to the accompanying figures using example embodiments. The illustration in the figures is schematic and highly simplified and not necessarily to scale.

FIG. 6 shows a data processing system.

FIG. 7 shows a medical imaging device.

DETAILED DESCRIPTION OF THE EXAMPLE EMBODIMENTS

Figure 1:
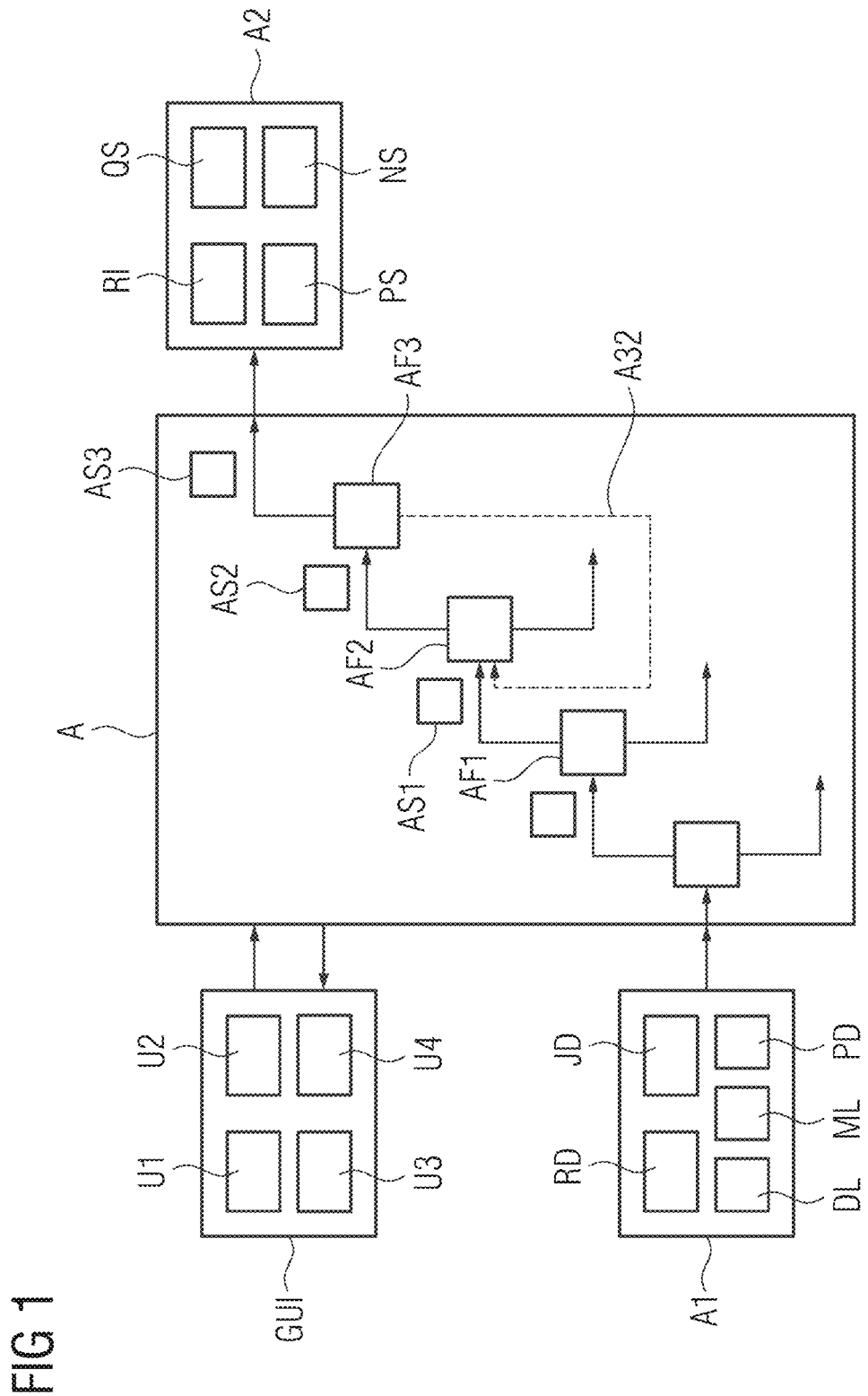
FIG. 1 shows a diagram illustrating the analysis of radiomics-related data using the assistance algorithm.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv)

source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment, the invention relates to a computer-implemented method for providing radiomics-related information, the method comprising receiving radiomics-related data, determining, based on the radiomics-related data and an assistance algorithm, a function for processing the radiomics-related data, calculating, based on the radiomics-related data and the function for processing the radiomics-related data, the radiomics-related information, and providing the radiomics-related information.

The assistance algorithm can be based on one or more machine learning algorithms. The assistance algorithm can be implemented in a software application. The assistance algorithm can be implemented based on statistical, machine learning and study design best practices, extensive experience and available expert knowledge.

In a further embodiment the method further comprises: generating, by a medical imaging device, the radiomics-related data.

In a further embodiment the method further comprises: displaying, by a display device, the radiomics-related information.

The radiomics-related data can comprise, for example medical imaging data, in particular medical imaging data related to an examination area of at least one patient. The examination area of the at least one patient can comprise, for example, at least one anatomical structure and/or at least one biomarker.

The assistance algorithm can act, for example, as an AI-based companion for the automated discovery and application of biomarkers. In this case, the assistance algorithm can be referred to as a Radiomics Imaging Biomarker Assistant (RIBA). Besides radiomics biomarkers, these may also include non-imaging-based biomarkers, e.g. other "omics" data.

It automatically analyzes the data to determine what kinds of analysis from a predefined pool are feasible. Given the type and distribution of data and which well-known pitfalls need to be taken care of in the scenario at hand. This can be accomplished by embedding an associated rule-base into the software. This rule-base can be given in a general machine-readable format such that it can be updated during maturation of the system.

Most steps involve a hybrid approach: both rules and the data at hand are used to determine whether a particular statistical method or sequence of methods is suited or not.

The assistance algorithm can be further based on techniques from meta learning, i.e. knowledge about learning procedures.

In another embodiment, a first user interaction element for a graphical user interface is generated based on the radiomics-related data and the assistance algorithm, wherein a first user input is received based on the first user interaction element, wherein the function for processing the radiomics-related data is determined further based on the first user input.

The first input can be related, for example, to at least one of the radiomics-related data, the function for processing the radiomics-related data or to the radiomics-related information.

In another embodiment, a first set of candidate functions for processing the radiomics-related data is calculated based on the radiomics-related data and the assistance algorithm, wherein the first user interaction element is indicative of each candidate function of the first set of candidate functions for processing the radiomics-related data, wherein a first function of the first set of candidate functions is determined based on the first user input, wherein the function for processing the radiomics-related data is determined further based on the first function.

The candidate function of a set of candidate functions, in particular of the first set of candidate functions, can differ from each other with respect to a class and/or with respect to parameters. Candidate function may be in a generalized form needing further parametrization before being applicable to the radiomics-related data. In particular, the function for processing the radiomics-related data can be a specific form of the first function.

As clinicians do often not know how to conduct studies with novel imaging technologies correctly, the assistance algorithm offers a guidance through the process.

In the preferred embodiment the results of this analysis are interactively presented to the user in a step-by-step guide, for example in form of a "wizard" tool, using simple explanations of the preferred options and the underlying reasons (akin to an "expert system"), such that the user is also able to improve their statistical expertise based on information that is directly applicable to their own studies.

In another embodiment, a first decision support information with respect to at least one candidate function of the first set of candidate functions is calculated based on the radiomics-related data and the assistance algorithm, wherein the first user interaction element is indicative of the first decision support information.

In another embodiment, a second set of candidate functions for processing the radiomics-related data is calculated based on the radiomics-related data, the assistance algorithm and the first function, wherein a second user interaction element for the graphical user interface is generated based on the radiomics-related data, the assistance algorithm and the first function, the second user interaction element being indicative of each candidate function of the second set of candidate functions for processing the radiomics-related data, wherein a second user input is received based on the second user interaction element, wherein a second function of the second set of candidate functions is determined based on the second user input, wherein the function for processing the radiomics-related data is determined further based on the second function.

In particular, the function for processing the radiomics-related data can be a specific form of the first function.

In another embodiment, each candidate function of the second set of candidate functions is a respective specific form of the first function.

In a further embodiment, a second decision support information with respect to at least one candidate function of the second set of candidate functions is calculated based on the radiomics-related data, the assistance algorithm and the first candidate function, wherein the second user interaction element is indicative of the second decision support information.

In another embodiment, a preliminary function for processing the radiomics-related data is determined based on the radiomics-related data and the assistance algorithm, wherein a preliminary radiomics-related information is calculated based on the radiomics-related data and the preliminary function for processing the radiomics-related data, wherein the first set of candidate functions for processing the radiomics-related data and/or the second set of candidate functions for processing the radiomics-related data is calculated further based on the preliminary radiomics-related information.

Preliminary results can alter the initially selected analysis branch leading to more accurate re-calculated results. If a specific preliminary result indicates that the analysis was not optimal, the assistance algorithm jumps back to the node in the tree where an error may have occurred.

One example is that a multivariate model may have too large confidence intervals of the odd's ratios, which indicates overfitting. Therefore, the backtracking mechanism jumps back to select a more stringent multiple comparison correction or alter the feature selection to a "rule of 50" instead of a "rule of 10". This modification can also be reflected in the publication draft.

In another embodiment, the function for processing the radiomics-related data is configured for generating a statistical diagram based on the radiomics-related data, wherein the radiomics-related information comprises the statistical diagram.

For example, the assistance algorithm can support clinical researchers doing statistical analysis, in particular not to make typical layman's errors when using automation tools.

The function for processing the radiomics-related data can be configured for generating high-quality publication-ready figures (e.g., segmentations and boxplots).

As the assistance algorithm can have access to the segmentations and results, it can automatically generate high-quality and paper-ready figures of the segmentations, the analyzed body region and the results. Visualizations may show univariate results by boxplots (quantiles, outliers) or Bland-Altman plots and multivariate models by the Receiver-Operating Characteristic (ROC) curve with confidence interval.

For survival analysis, Kaplan-Meier curves are automatically generated with a separation in predicted high- and low-risk curve. Also, a CONSORT diagram may be generated based on the Data Assessment done before. Statistics for the given data frame are extracted automatically, e.g. how many entries are missing for each respective feature analyzed.

Also an appropriate data imputation method is selected for the data given. The semantic of the given label is derived automatically, e.g. a label named "survival" with continuous values induces a survival analysis with censored data. Automated, the data can be curated after best practices In particular, the assistance algorithm is configured for curation and/or imputation of the radiomics-related data. Calculations can be based on the curated and/or imputated data.

In another embodiment, the function for processing the radiomics-related data is configured for generating a publication draft based on the radiomics-related data, wherein the radiomics-related information comprises the publication draft.

Based on an initial selection of the target journal, the analysis is given a journal-specific focus. For example, a first journal may prefer more conservative statistical analyses, while a second journal is open for radiomics analyses, but only publishes publications with external validation cohort.

The sections of the paper draft are generated according to the current journal guidelines.

Seeing as how there are established recommendations on how to report statistical results in scientific publications (which unfortunately are often not honored either), the companion system can also suggest the proper, "paper-ready" wording for any of the results found. The focus of a specific journal can be selected (e.g. radiological or clinical). This influences the wording of the publication As further information on the analyzed data is often already available in the prototype (e.g. number of patients/samples, scan and reconstruction parameters, names and thus—to a certain extent—semantics of the employed features), the description of the experiments required in a paper can be automated to some degree as well. This helps to avoid errors and further supports the time-efficient realization of high-quality clinical publications.

The key to this functionality of our system is to store all analysis results in a general structured way such that different rule-based use cases as described above can easily be put into action.

Also, information such as used scan protocol and patient characteristics are automatically extracted from the DICOM tags of the study cohort or from data entered manually.

Also, the references identified in the Novelty Estimation step are listed here to provide an overview of relevant literature. The performed curation and assessment steps are also documented. Optionally, the Study Quality Estimation may also be entered.

If more than one branch is processed (which is possible if the user chooses their own branches), the analyses may be compared when they are near each other in the tree. It is also possible to do both a statistical and a machine learning based analysis on the data. Then, the results are given independently without comparison.

Although the optimal branches are proposed automatically, the results for other branches can be entered in the manuscript manually by selecting them from the tree. However, the Study Quality may suffer the user may be given a warning that the analysis is not canonical.

In another embodiment, journal-specific data are received, wherein the function for processing the radiomics-related data is determined further based on the journal-specific data.

The journal-specific data can be related, for example, to the focus and/or style of a journal, in which the radiomics-related information, in particular comprising a publication draft, is intended to be published.

In particular, the assistance algorithm can be configured for determining the function for processing the radiomics-related data further based on the journal-specific data.

For example, the first decision support information and/or the second decision support information can be calculated based on the journal specific data.

In another embodiment, at least one data label with respect to the radiomics-related data is received, wherein at least one method label with respect to the function for processing the radiomics-related data is received, wherein an access to a publication database is received, wherein a set of publications based on the at least one data label, the at least one method label, the access to the publication database and the assistance algorithm is determined, wherein the function for processing the radiomics-related data is determined further based on the set of publications.

In particular, the assistance algorithm can be configured for determining the function for processing the radiomics-related data further based on the set of publications.

Information regarding the set of publications can be provided, for example in form of a list being indicative of each publication of the set of publications.

For example, the assistance algorithm can recommend that the user specify meaningful names for their labels, for example with the help of the graphical user interface. If such names are given, an automated literature search is started searching publications for the respective combination of the used method and the label.

If there are many publications with high citation number for the respective combination of label and analysis method (or a similar method), the novelty score decreases.

For example, a novelty score can be calculated based on the at least one data label, the at least one method label, the set of publications and the assistance algorithm. The novelty score can be provided.

In another embodiment, a quality score is calculated based on the radiomics-related data, the function for processing the radiomics-related data, the radiomics-related information and the assistance algorithm, wherein the quality score is provided.

Study quality is assessed, to give the user easy understandable metrics to estimate the chances of their study to be published in a high impact journal.

This integrates concepts of the radiomics quality score but also calculations of statistical power and quality factors in statistics (Brier Score etc.). Factors that are analyzed here are for example the study size, if an external validation cohort was given, if the suggested analysis was accepted or a different branch of the RIBA Analytics Tree was chosen which may be non-canonical.

Further information regarding the study quality may be inquired from the user directly based on the graphical user interface ("If applicable, please give an inter-reader agreement between the segmentations").

In another embodiment the invention relates to data processing system for providing radiomics-related information, comprising a receiving interface, configured for receiving radiomics-related data, a determining unit, configured for determining, based on the radiomics-related data and an assistance algorithm, a function for processing the radiomics-related data, a calculating unit, configured for calculating, based on the radiomics-related data and the function for processing the radiomics-related data, the radiomics-related information, a providing interface, configured for providing the radiomics-related information.

In particular, the data processing system can be configured for carrying out a method for providing radiomics-related information according to any of the disclosed embodiments.

In another embodiment the invention relates to a computer program comprising instructions which, when the program is executed by a data processing system, cause the data processing system to carry out the method of one of the disclosed embodiments.

In another embodiment the invention relates to a computer-readable medium comprising instructions which, when executed by a data processing system, cause the system to carry out the method of one of the disclosed embodiments.

Herewith, in at least one embodiment, a medical imaging device is disclosed, the medical imaging device comprising a data processing system for providing radiomics-related information according to one or more of the disclosed embodiments. The medical imaging device may be, for example, a computed tomography (CT) device or a magnetic resonance imaging (MRI) device or a combination of different medical imaging modalities, for example, a PET-CT-imaging device. The medical imaging data can be acquired, for example, by the medical imaging device. The medical imaging data can comprise, for example, computed tomography medical imaging data and/or magnetic resonance medical imaging data.

The data processing system can be, for example, server/cloud-based or local or a hybrid solution. The preferred embodiment of the system is server/cloud-based, enabling direct global updates of rule-bases, guidelines, best practices and software components for all users. Server-based updates also guarantee to provide the customer with explanations and guidance for the novel imaging technology and the correct evaluation of its value.

Other embodiments involve the system running locally at a customer's site or hybrids between local and remote deployments.

All parts of the system may be updated server-based, if a new trend in analysis methods is obvious.

If a more suitable method is identified or the scope of a journal changes, the RIBA Analytics Tree can change the chosen branch after a server-update. This way, also a correct conduction of a study with novel imaging technologies can be guaranteed.

The assistance algorithm enables the translation of statistical, machine learning and study design best practices into an AI-based companion system with an emphasis to promote novel imaging technologies (such as photon counting). Suitable biomarker analyses can be implemented in the assistance algorithm by making use of extensive experience and available expert knowledge with regard to which analysis performs well on which kinds of data sets and how novel imaging technologies can be compared with established ones.

This results in very strong benefits, for example in cost reduction, customer retention and faster dissemination of key technologies among customers.

The cost reduction can be explained by the fact that the work and expense of managing a clinical trial, e.g. through global collaboration managers but also through R&D, is significantly reduced.

Customer retention is achieved as the assistance algorithm makes it very easy for hospitals to evaluate an imaging biomarker study. Normally these employ statisticians, machine learning experts or physicists for assistance, which often do not explain their decisions properly. Because of the assistance algorithm's explainability in decision making and the possibility to intervene with the analysis, the customer feels in the driver's seat when conducting his study.

Finally, the establishment of new imaging technologies benefits from the assistance algorithm because a, it guides the customer in an explainable way through the execution of a study with new technologies, therefore training him in the use of the new technology, as well as b, through the shorter time to publication. Faster, more and higher quality publications mean scalable advertising and increased visibility for novel imaging technologies such as photon counting.

Any of the algorithms mentioned herein, in particular the assistance algorithm and/or the function for processing the radiomics-related data, can be based on one or more of the following architectures: convolutional neural network, deep belief network, random forest, deep residual learning, deep reinforcement learning, recurrent neural network, Siamese network, generative adversarial network or auto-encoder. In particular, the trained machine learning algorithm can be embodied as a deep learning algorithm, in particular as a deep convolutional neural network.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing an action of a method may be carried out in a processor.

Data, in particular the radiomics-related data, can be received, for example, by receiving a signal that carries the data and/or by reading the data from a computer-readable medium and/or by receiving an input through a user interface. Data, in particular, the radiomics-related information can be provided, for example, by transmitting a signal that carries the data and/or by writing the data into a computer-readable medium and/or by displaying the data on a display.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described units are merely preferred example embodiments of the invention and that the invention can be varied by a person skilled in the art, without departing from the scope of the invention as it is specified by the claims.

FIG. 1 shows a diagram illustrating the analysis of radiomics-related data RD using the assistance algorithm A.

The input A1 for the assistance algorithm A comprises the radiomics-related data RD, the journal-specific data JD, the data label DL, the method label ML and the access to a publication database PD. In addition, the input A1 can comprise any other data, for example "omics" data other than radiomics-related data. The output A2 of the assistance algorithm A comprises the radiomics-related information, the set of publications PS, the novelty score NS and the quality score QS.

The journal-specific data JD are received, wherein the function for processing the radiomics-related data RD is determined further based on the journal-specific data JD.

The data label DL with respect to the radiomics-related data RD is received. The method label ML with respect to the function for processing the radiomics-related data RD is received. An access to a publication database PD is received, wherein a set of publications PS based on the at least one data label DL, the at least one method label ML, the access to the publication database PD and the assistance algorithm A is determined, wherein the function for processing the radiomics-related data RD is determined further based on the set of publications PS.

For determining the function for processing the radiomics-related data, the assistance algorithm follows tree-like structure (also referred to as the Analytics Tree). At each of the nodes AF1, AF2 and AF3 a respective set of candidate functions is calculated.

In an interactive mode, the assistance algorithm proposes, at each of the nodes AF1, AF2 and AF3, the respective analysis based on his current understanding of the data and asks the user if he wants to follow it, therefore making it interactive. The assistance algorithm A interactively navigates the user through the analysis. Here, suggestions are given and explained with links to the respective literature. The user can override those suggestions.

The advantage of this procedure is that it is computationally efficient as only one branch of the Analytics Tree is processed at a time. At each step, the user can choose any of the suggested options to advance to the next steps in the analysis. In that manner, it is ensured that analysis workflows are followed which adhere to statistical best practices and scientific guidelines.

In a fully automated mode, the assistance algorithm can compute the whole Analytics Tree without any user input after the fully automated computation is triggered. In the fully automated case, the branch of the tree that corresponds to the chain of decisions recommended by the system is pre-computed automatically. It is also possible to select further branches to be computed additionally, which may be non-optimal, but also of interest to the user. For exhaustive analysis, there may also be an option to trigger pre-computation of the whole tree (time-intensive) such that each results section of the tree is accessible. The assistance algorithm chooses the possible options based on the characteristics of the data as well as the aforementioned best practices and guidelines. The fully automated computation can also be triggered after some steps of the analysis have been already performed in the interactive mode.

In both modes, all decisions and branches are made explainable to the user by hyperlinks to the respective literature. The study quality is evaluated. This is especially important if the branch of the tree is chosen manually.

At each node of the tree, information regarding a decision support and/or decision rationale is calculated and made available to the user. For example, when in interactive mode at node AF1, the assistance algorithm makes the decision support information U10 available to the user through the graphical user interface GUI. After the first function of the first set of candidate functions has been determined based on the first user input, the decision rationale AS1 for determining the first function is stored and can be shown to the user in the graphical user interface. Further decision rationales AS2 and AS3 are handled similarly.

A preliminary function for processing the radiomics-related data RD is determined based on the radiomics-related data RD and the assistance algorithm A, wherein a preliminary radiomics-related information is calculated based on the radiomics-related data RD and the preliminary function for processing the radiomics-related data RD, wherein the first set of candidate functions for processing the radiomics-related data RD and/or the second set of candidate functions for processing the radiomics-related data RD is calculated further based on the preliminary radiomics-related information.

This Backtracking is illustrated by the dashed line A32.

At each leaf of the tree, the results for the corresponding branch are shown. For example, for the statistics branch, the univariate results, selected features and multivariate results may be shown together with the used test (e.g. T-test, Mann-Whitney). The multivariate model is evaluated by many different metrics, but the most important ones are again proposed, i.e. ROC-AUC, Odds Ratios and Brier Score. The user receives the results of the statistical analysis, including but not limited to re-usable statistical and machine learning models as well as diagrams and tables obtained with them.

Through hyperlinks U2, U3, U4 in the graphical user interface GUI, the assistance algorithm gives proposals on his current understanding of the data, best practices and status-quo literature, in particular with a focus towards the journal for which the manuscript should be submitted.

A short tutorial for the imaging technology and the correct study design can be shown in the graphical user interface. Then, to evaluate the added value of e.g. multispectral imaging, the assistance algorithm can automatically compare branches of single-energy images with branches of multispectral images with explanation of the procedure and why it is done. This leads to a deeper understanding of the procedure. An easy-to-publish and high-quality study can be therefore provided.

Figure 2:
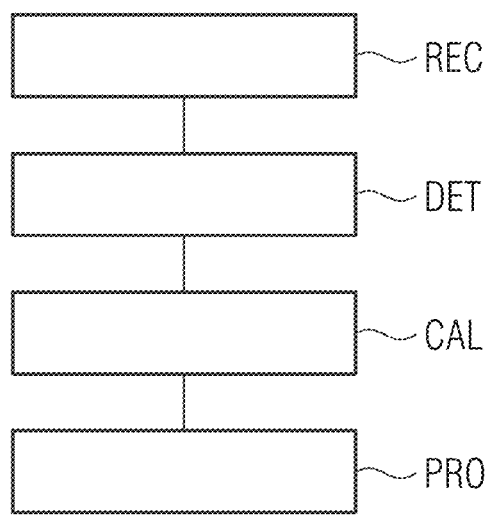
FIG. 2 shows a diagram illustrating a method for providing radiomics-related information.

FIG. 2 shows a diagram illustrating a computer-implemented method for providing radiomics-related information RI, the method comprising receiving REC radiomics-related data RD, determining DET, based on the radiomics-related data RD and an assistance algorithm A, a function for processing the radiomics-related data RD, calculating CAL, based on the radiomics-related data RD and the function for processing the radiomics-related data RD, the radiomics-related information RI, providing PRO the radiomics-related information RI.

Figure 3:
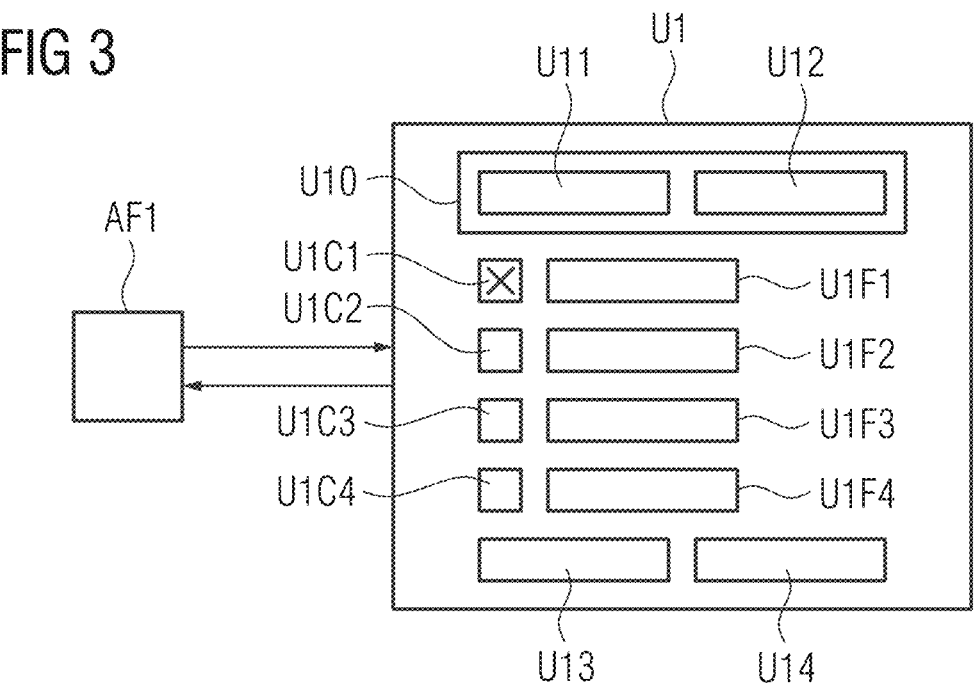
FIG. 3 show a first user interaction element for a graphical user interface.

FIG. 3 show a first user interaction element U1 for a graphical user interface GUI. The user interaction element U1 is displayed to the user through the graphical user interface GUI.

A first user interaction element U1 for a graphical user interface GUI is generated based on the radiomics-related data RD and the assistance algorithm A, wherein a first user input is received based on the first user interaction element U1, wherein the function for processing the radiomics-related data RD is determined further based on the first user input.

A first set of candidate functions for processing the radiomics-related data RD is calculated based on the radiomics-related data RD and the assistance algorithm A, wherein the first user interaction element U1 is indicative of each candidate function of the first set of candidate functions for processing the radiomics-related data RD, wherein a first function of the first set of candidate functions is determined based on the first user input, wherein the function for processing the radiomics-related data RD is determined further based on the first function.

A first decision support information U10 with respect to at least one candidate function of the first set of candidate functions is calculated based on the radiomics-related data RD and the assistance algorithm A, wherein the first user interaction element U1 is indicative of the first decision support information U10.

A second set of candidate functions for processing the radiomics-related data RD is calculated based on the radiomics-related data RD, the assistance algorithm A and the first function, wherein a second user interaction element U2 for the graphical user interface GUI is generated based on the radiomics-related data RD, the assistance algorithm A and the first function, the second user interaction element being indicative of each candidate function of the second set of candidate functions for processing the radiomics-related data RD, wherein a second user input is received based on the second user interaction element U2, wherein a second function of the second set of candidate functions is determined based on the second user input, wherein the function for processing the radiomics-related data RD is determined further based on the second function.

Each candidate function of the second set of candidate functions is a respective specific form of the first function.

The decision support information U10 comprises a first hyperlink U11 to analysis details and a second hyperlink U12 to the literature that has been determined by the assistance algorithm as relevant for determining the first set of candidate functions and/or the first function. Literature for further understanding of the proposed branch of the tree can be linked in the decision support information U10. For example, the multiple testing correction and the choice of the suitable univariate statistical test can be explained in the decision support information U10.

One or more functions of the first set of candidate functions U1F1, U1F2, U1F3 and U1F4 can be selected using the respective checkboxes U1C1, U1C2, U1C3 and U1C4. Selection of multiple candidates can be allowed, resulting in multiple algorithm outputs. The first user interaction element U1 comprises navigation elements for navigating the Analytics tree backwards U13 or forwards U14. Navigation paths can be displayed in different colors, depending, for example, on a degree, to which this path is recommended by the assistance algorithm. A model comparison can be generated automatically based on the recommended analysis and further user-initiated analysis. Proposed and/or user-selected branches of the analytics tree can be adapted to the respective journal.

Therefore the assistance algorithm helps with a very fast, correct and high-quality study that results in a faster, scalable advertisement of novel technologies.

Figure 4:
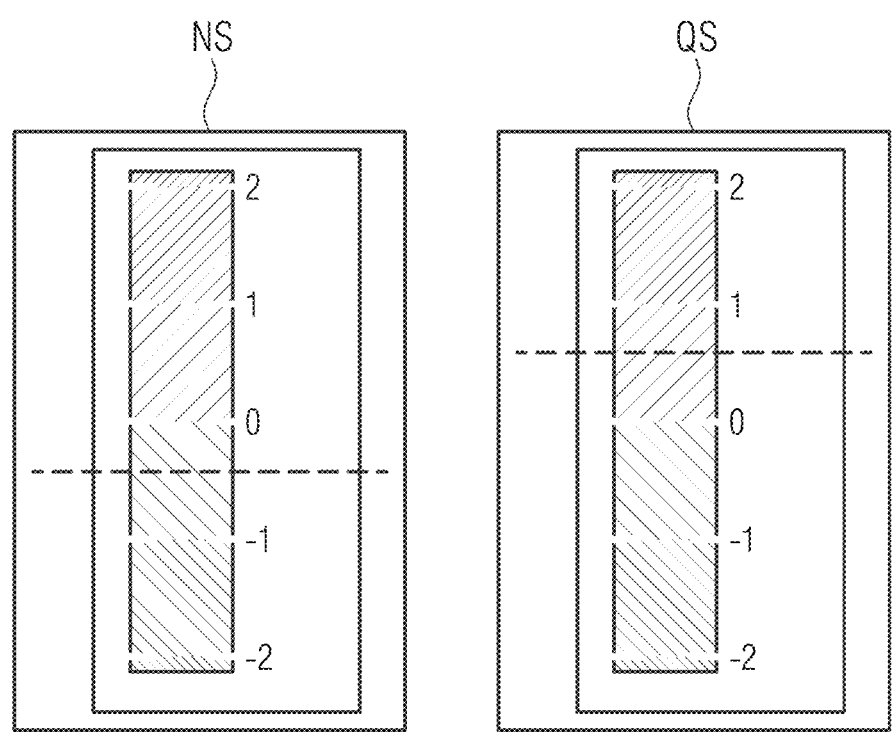
FIG. 4 shows an example of a novelty score and an example of a quality score.

FIG. 4 shows an example for a novelty score NS and an example for a quality score QS, each displayed based on a color scale. A quality score QS based on the radiomics-related data RD, the function for processing the radiomics-related data RD, the radiomics-related information RI and the assistance algorithm A is calculated, wherein the quality score QS is provided.

Figure 5:
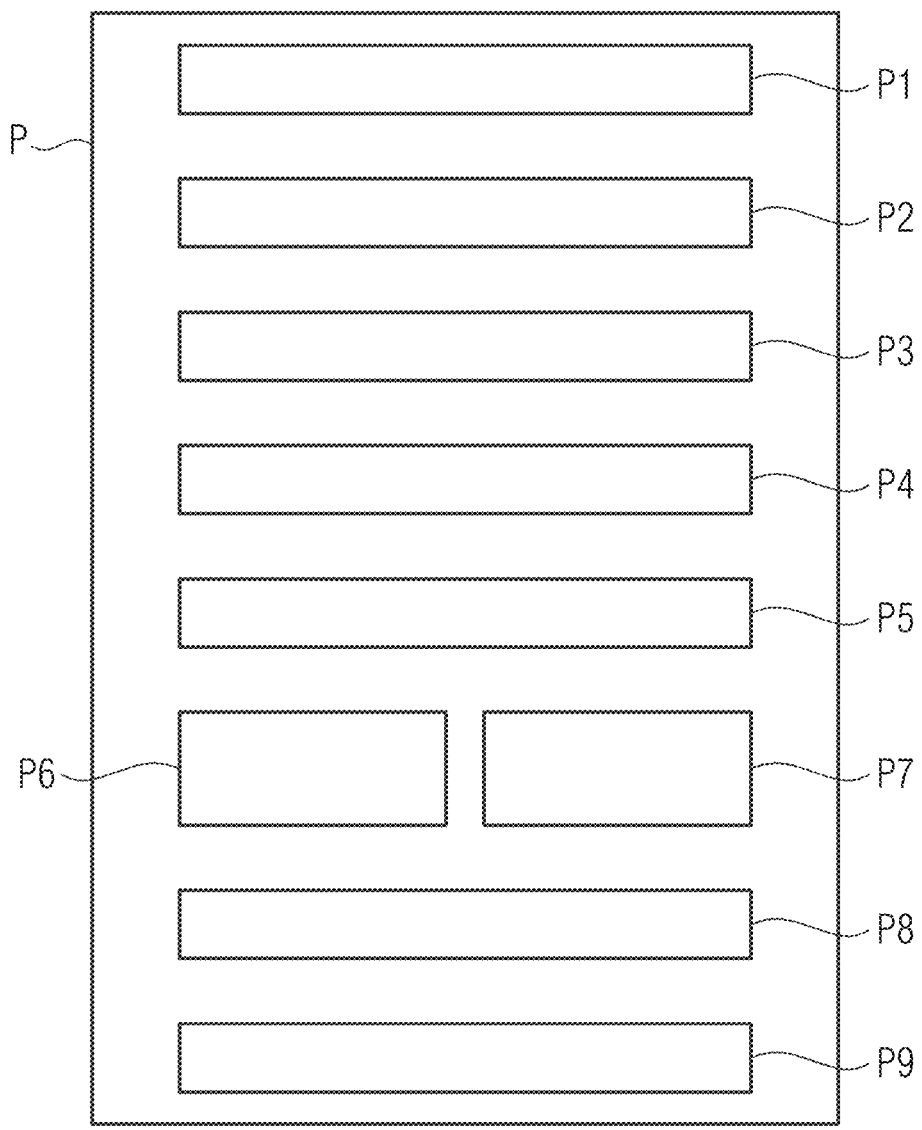
FIG. 5 shows a publication draft.

FIG. 5 shows a publication draft P. The function for processing the radiomics-related data RD is configured for generating a publication draft P based on the radiomics-related data RD, wherein the radiomics-related information RI comprises the publication draft P.

The publication draft P is generated based on the template and the scope of the journal according to the journal-specific data JD. The assistance algorithm can extract data required for the publication such as scan date interval, number of included patients and CONSORT diagram data automatically from the radiomics-related data.

The publication draft comprises the publication title P1, the scientific background P2 based on the set of publications PS, the introduction to the present study P3, the section regarding materials and methods P4, the section regarding results P5, figures P6, diagrams P7, tables P8 and literature references P9 based on the set of publications PS.

FIG. 6 shows the data processing system 3 for providing radiomics-related information RI, comprising a receiving interface 3REC, configured for receiving REC radiomics-related data RD, a determining unit 3DET, configured for determining DET, based on the radiomics-related data RD and an assistance algorithm A, a function for processing the radiomics-related data RD, a calculating unit 3CAL, configured for calculating CAL, based on the radiomics-related data RD and the function for processing the radiomics-related data RD, the radiomics-related information RI, a providing interface 3PRO, configured for providing PRO the radiomics-related information RI.

In particular, the data processing system can be configured for carrying out a method for providing radiomics-related information according to any of the disclosed embodiments.

FIG. 7 shows a medical imaging device 1, comprising the computer 30 with the data processing system 3, the processor 33, the computer-readable medium 31 and the data input/output interface 32. The medical imaging device 1 further comprises a display 39, for example in form of a touch screen, displaying the user interface GUI, and a user input device 38. Each of the receiving interface 3REC, the determining unit 3DET, the calculating unit 3CAL and the providing interface 3PRO could be realized by the computer 30. The processor 33 can form the determining unit 3DET as well as the calculating unit 3CAL.

In this example, the medical imaging device 1 is a computed tomography device with a gantry 20, 21, 22, a radiation source 26, a radiation detector 28 for detecting the radiation 27, a bore 9, an acquisition area 4 and a patient handling system 10, 11, 12 for handling the patient 13.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing radiomics-related information, the computer-implemented method comprising
   receiving radiomics-related data;
   determining, based on the radiomics-related data and an assistance algorithm, a function for processing the radiomics-related data;
   calculating, based on the radiomics-related data and the function for processing the radiomics-related data, the radiomics-related information; and
   providing, to a user, the radiomics-related information including at least one of a statistical diagram based on the radionics-related data,
   a publication draft based on a scope of a journal according to journal-specific data used to determine the function for processing the radiomics-related data,
   a novelty score indicating a citation number for a combination of a label and an analysis method of the function for processing the radiomics-related data, based on a set of publications, or
   a quality score indicating an estimated chance of a study based on the radiomics-related information to be published in a high impact journal.

2. The computer-implemented method of claim 1, further comprising:
   generating a first user interaction element for a graphical user interface based on the radiomics-related data and the assistance algorithm; and
   receiving a first user input based on the first user interaction element,
   wherein the determining the function for processing the radiomics-related data is further based on the first user input.

3. The computer-implemented method of claim 2, further comprising:
   calculating a first set of candidate functions for processing the radiomics-related data based on the radiomics-related data and the assistance algorithm; and
   determining a first function of the first set of candidate functions based on the first user input,
   wherein the first user interaction element indicates each candidate function of the first set of candidate functions for processing the radiomics-related data, and
   wherein the determining the function for processing the radiomics-related data is further based on the first function.

4. The computer-implemented method of claim 2, further comprising:
   calculating a first decision support information, with respect to at least one candidate function of the first set of candidate functions, based on the radiomics-related data and the assistance algorithm,
   wherein the first user interaction element indicates the first decision support information.

5. The computer-implemented method of claim 2, further comprising:
   calculating a second set of candidate functions for processing the radiomics-related data based on the radiomics-related data, the assistance algorithm, and the first function;
   generating a second user interaction element for the graphical user interface based on the radiomics-related data, the assistance algorithm, and the first function, the second user interaction element indicating each candidate function of the second set of candidate functions for processing the radiomics-related data;
   receiving a second user input based on the second user interaction element; and
   determining a second function of the second set of candidate functions based on the second user input,
   wherein the determining the function for processing the radiomics-related data is further based on the second function.

6. The computer-implemented method of claim 5,
   wherein each candidate function of the second set of candidate functions is a respective specific form of the first function.

7. The computer-implemented method of claim 3, further comprising:

determining a preliminary function for processing the radiomics-related data based on the radiomics-related data and the assistance algorithm; and calculating preliminary radiomics-related information based on the radiomics-related data and the preliminary function for processing the radiomics-related data, wherein the calculating the first set of candidate functions for processing the radiomics-related data for processing the radiomics-related data includes calculating the first set of candidate functions further based on the preliminary radiomics-related information.

8. The computer-implemented method of claim 1,
wherein the function for processing the radiomics-related data is configured to generate the statistical diagram based on the radiomics-related data, and
wherein the radiomics-related information includes the statistical diagram.

9. The computer-implemented method of claim 1,
wherein the function for processing the radiomics-related data is configured to generate the publication draft based on the radiomics-related data, and
wherein the radiomics-related information includes the publication draft.

10. The computer-implemented method of claim 1, further comprising:
receiving the journal-specific data, and
wherein the determining the function for processing the radiomics-related data is further based on the journal-specific data.

11. The computer-implemented method of claim 1, further comprising:
receiving at least one data label with respect to the radiomics-related data;
receiving at least one method label with respect to the function for processing the radiomics-related data;
receiving an access to a publication database; and
determining a set of publications based on the at least one data label, the at least one method label, the access to the publication database, and the assistance algorithm,
wherein the determining the function for processing the radiomics-related data is further based on the set of publications.

12. The computer-implemented method of claim 11, further comprising:
calculating the novelty score based on the at least one data label, the at least one method label, the set of publications and the assistance algorithm,
wherein the radiomics-related information includes the novelty score.

13. The computer-implemented method of claim 1, further comprising:
calculating the quality score based on the radiomics-related data, the function for processing the radiomics-related data, the radiomics-related information, and the assistance algorithm,
wherein the radiomics-related information includes the quality score.

14. A data processing system for providing radiomics-related information, comprising:
a memory storing computer-executable instructions; and
at least one processor configured to execute the computer-executable instructions to cause the system to
receive radiomics-related data,
determine, based on the radiomics-related data and an assistance algorithm, a function for processing the radiomics-related data, calculate, based on the radiomics-related data and the function for processing the radiomics-related data, the radiomics-related information, and provide, to a user via an interface, the radiomics-related information including at least one of a statistical diagram based on the radiomics-related data,
a publication draft based on a scope of a journal according to journal-specific data used to determine the function for processing the radiomics-related data,
a novelty score indicating a citation number for a combination of a label and an analysis method of the function for processing the radiomics-related data, based on a set of publications, or
a quality score indicating an estimated chance of a study based on the radiomics-related information to be published in a high impact journal.

15. A non-transitory computer program product storing instructions which, when the program is executed by a data processing system, cause the data processing system to carry out the method of claim 1.

16. A non-transitory computer-readable medium storing instructions which, when executed by a data processing system, cause the system to carry out the method of claim 1.

17. The computer-implemented method of claim 3, further comprising:
calculating a first decision support information, with respect to at least one candidate function of the first set of candidate functions, based on the radiomics-related data and the assistance algorithm,
wherein the first user interaction element indicates the first decision support information.

18. The computer-implemented method of claim 3, further comprising:
calculating a second set of candidate functions for processing the radiomics-related data based on the radiomics-related data, the assistance algorithm, and the first function;
generating a second user interaction element for the graphical user interface based on the radiomics-related data, the assistance algorithm, and the first function, the second user interaction element indicating each candidate function of the second set of candidate functions for processing the radiomics-related data;
receiving a second user input based on the second user interaction element; and
determining a second function of the second set of candidate functions based on the second user input,
wherein the determining the function for processing the radiomics-related data is further based on the second function.

19. The computer-implemented method of claim 18,
wherein each candidate function of the second set of candidate functions is a respective specific form of the first function.

20. The computer-implemented method of claim 2,
wherein the function for processing the radiomics-related data is configured to generate a statistical diagram based on the radiomics-related data, and
wherein the radiomics-related information includes the statistical diagram.

21. The computer-implemented method of claim 2,
wherein the function for processing the radiomics-related data is configured to generate the publication draft based on the radiomics-related data, and
wherein the radiomics-related information includes the publication draft.

22. The computer-implemented method of claim 2, further comprising:

receiving the journal-specific data, wherein the determining the function for processing the radiomics-related data is further based on the journal-specific data.

23. The computer-implemented method of claim 2, further comprising:

receiving at least one data label with respect to the radiomics-related data;

receiving at least one method label with respect to the function for processing the radiomics-related data;

receiving an access to a publication database; and determining a set of publications based on the at least one data label, the at least one method label, the access to the publication database, and the assistance algorithm, wherein the determining the function for processing the radiomics-related data is further based on the set of publications.

24. The computer-implemented method of claim 23, further comprising:

calculating the novelty score based on the at least one data label, the at least one method label, the set of publications, and the assistance algorithm, wherein the novelty score.

25. The computer-implemented method of claim 2, further comprising:

calculating the quality score based on the radiomics-related data, the function for processing the radiomics-related data, the radiomics-related information, and the assistance algorithm, wherein the radiomics-related information includes the quality score.

* * * * *

UNITED STATES PATENT AND TRADEMARK OFFICE
CERTIFICATE OF CORRECTION

PATENT NO. : 11,954,178 B2
APPLICATION NO. : 17/462140
DATED : April 9, 2024
INVENTOR(S) : Alexander Muehlberg et al.

It is certified that error appears in the above-identified patent and that said Letters Patent is hereby corrected as shown below:

In the Claims

Claim 1 should read:
1. A computer-implemented method for providing radiomics-related information, the computer-implemented method comprising
    receiving radiomics-related data;
    determining, based on the radiomics-related data and an assistance algorithm, a function for processing the radiomics-related data;
    calculating, based on the radiomics-related data and the function for processing the radiomics-related data, the radiomics-related information; and
    providing, to a user, the radiomics-related information including at least one of
        a statistical diagram based on the radiomics-related data,
        a publication draft based on a scope of a journal according to journal-specific data used to determine the function for processing the radiomics-related data,
        a novelty score indicating a citation number for a combination of a label and an analysis method of the function for processing the radiomics-related data, based on a set of publications, or
        a quality score indicating an estimated chance of a study based on the radiomics-related information to be published in a high impact journal.

Signed and Sealed this
Third Day of December, 2024

Katherine Kelly Vidal
*Director of the United States Patent and Trademark Office*